United States Patent [19]

Nilsson

[11] Patent Number: 5,405,752
[45] Date of Patent: Apr. 11, 1995

[54] ENZYME CONJUGATE PREPARED WITH INSOLUBLE NONOPARTICLE

[76] Inventor: Kurt G. I. Nilsson, Andjaktsv. 6, S-222 53 Lund, Sweden

[21] Appl. No.: 185,213

[22] Filed: Jan. 14, 1994

Related U.S. Application Data

[63] Continuation of Ser. No. 548,976, Aug. 1, 1990, abandoned.

[30] Foreign Application Priority Data

Oct. 3, 1988 [SE] Sweden ................... 8803496

[51] Int. Cl.$^6$ ............................................. G01N 33/53
[52] U.S. Cl. ........................................ 435/7.94; 435/5; 435/7.95; 436/518; 436/527; 436/531; 436/829
[58] Field of Search .................. 435/5, 7.9, 7.92, 7.94, 435/7.95; 436/518, 527, 531, 829

[56] References Cited

U.S. PATENT DOCUMENTS

| | | | |
|---|---|---|---|
| 4,267,235 | 5/1981 | Rembaum et al. | 428/207 |
| 4,415,665 | 11/1983 | Mosbach et al. | 435/179 |
| 4,434,150 | 2/1984 | Azad et al. | 424/1.1 |
| 4,552,839 | 11/1985 | Gould et al. | 422/56 |
| 4,698,263 | 10/1985 | Wagner et al. | 428/402.2 |
| 4,918,009 | 4/1990 | Nilsson | 435/73 |

FOREIGN PATENT DOCUMENTS 077671 4/1983 European Pat. Off. .
155224 9/1985 European Pat. Off. .

OTHER PUBLICATIONS

Nilsson et al., Methods in Enzymology 104: 56–69, 1984.

*Primary Examiner*—Esther M. Kepplinger
*Assistant Examiner*—Donna C. Wortman
*Attorney, Agent, or Firm*—Beveridge, DeGrandi, Weilacher & Young

[57] ABSTRACT

The invention relates to a reagent consisting of at least one enzyme and at least one other substance, which are covalently or noncovalently bound to a particle, which is smaller than or is equal to 1000 Angstrom in diameter. The invention also relates to method and use of the reagent for determination or studies of a cell or a virus or another component in a sample. According to the invention, these determinations are made with for example some ELISA-technique (competitive, sandwich, etc), employing the reagent preferably in the form of a suspension in buffered water, instead of and in the same way as described for soluble enzyme conjugates. The substance can be antibody, a lectin, avidin or an antigen, the enzyme can be for example peroxidase, alcaline phosphatase, and the particle can be an inorganic or an organic polymeric compound or a combination thereof, as, for example, tresyl-activated glycerylpropyl-silica.

11 Claims, No Drawings

ENZYME CONJUGATE PREPARED WITH INSOLUBLE NONOPARTICLE

This application is a continuation of application Ser. No. 07/548,976, filed Aug. 1, 1990, abandoned, which application is entirely incorporated herein by reference.

The present invention relates to a new type of reagent to be used in the determination of a cell, a virus or another component of a test and to the use of the reagent in diagnostical, clinical, histochemical or microscopical applications.

BACKGROUND

Chemical analysis based on specific biological affinity between receptor and ligand, as for example between antibody and antigen, between lectin and carbohydrate, between nucleotides etc. has been used for several years and their use in the separation and determination of cells, virus or other components in samples has increased lately. Examples of this are analysis based on antibodies, i.e. the immunotechniques. Antibodies are here used for the specific binding of the analyte in the sample. Detection of antibody-ligand complex or of free antibody can be done in several ways. In the so called radioimmunoassay, RIA, radioactively marked antibodies or ligands are used, but also for example bacteriophages, free radicals, fluorescent or luminescent groups, different enzymes and particles have been used as markers in immunoassays (see e.g. Ngo and Lenhoff, editors, Enzyme-mediated Immunoassay, pages 3–32, Plenum Press, 1985, ref. 1). RIA has however dominated. In spite of the advantages of RIA, disadvantages as for example the instability of several gamma-emitters and the health hazards by the synthesis and the handling of the radioactive ligands or antibodies have led to the gradual replacement of the radioactive markers by other types of markers. Especially enzyme immunoassay (EIA; ref. 1 and Engvall, Meth. Enzymol., 70, pages 419–439; ref. 2) has turned out to have advantages and is more and more used. EIA is divided into homogeneous and heterogeneous EIA. Heterogeneous EIA, which includes ELISA (enzyme linked immunosorbent assay) is based on the same principles as RIA and very often gives similar sensitivity and specificity. These immunotechniques and techniques based on other types of biospecific interactions for analysis of cells, virus or other components in samples, require methods for the conjugation of receptor or ligand to any type of marker substance (e.g. an enzyme or a radioactive substance). Even if several such methods based on chemical reagents are described in the literature (for example glutaraldehyde, periodate or thiol substances; see O'Sullivan and Marks Meth. Enzymol. vol. 73, pages 147–166, ref. 3, ref. 2 and other relevant articles in Meth. Enzymol., volumes 70, 73 and 92), they all have their drawbacks. It is for instance difficult with existing techniques to produce, reproducible and controllable, for example enzyme-antigen, enzyme-antibody or enzyme-lectin conjugates and other types of enzyme-ligand or enzyme-receptor conjugates. One obtains conjugates which are heterogeneous in size and structure. Furthermore, conjugation may cause decreased enzyme activity or specificity of the ligand or receptor. Furthermore, even if the sensitivity often is sufficient, EIA is in many cases limited by insufficient sensitivity. One has tried to increase the sensitivity by using more or less complicated systems as avidin-biotin (Kendall et al, J. Immunol. Meth., vol. 56, page 329, 1983, ref. 4, see also ref. 1–3 and relevant articles in Meth. Enzymol.) or so called enzyme-cascades (Self, U.S. patent application Ser. No. 307,600; ref. 5).

A more simple system utilises soluble, oligomeric enzyme coupled to antibody. Leary et al, Proc. Nat. Acad. Sci., vol 80, page 4045, 1983; ref. 6). Even if these so called amplification techniques are useful in several applications, they have their limitations and disadvantages and Ngo mentions in a review that increased sensitivity of EIA and better methods for the preparation of enzyme-ligand or enzyme-receptor conjugates are desirable.

One of the objects of this invention is to reduce these disadvantages by EIA and a simple method to form enzyme-antigen, enzyme-antibody or enzyme-lectin conjugates, as well as conjugates between enzyme and other types of ligands or receptors, are described. Furthermore, it is described how this reagent can be used for the detection of a cell, a virus or another component in a sample and how an increased sensitivity compared to earlier methods can be reached by using the reagent according to the invention.

These and other aims can be reached, according to the invention, by covalent or noncovalent binding of enzyme and antibody or enzyme and lectin or enzyme and antigen (or in general, enzyme and ligand or receptor) to suitable type of particles, which are insoluble in the medium (usually buffered water) used in the conjugation reaction to the particle and in the determination of the analyte, and, furthermore, by using thus formed reagent, instead of and in the same way as previously described enzyme conjugates, for the specific detection of a cell, a virus or another component in a test.

By changing the size of the particle, the chemical and physical structure, type of surface (hydrophobic, hydrophilic, with or without reactive groups), enzyme, antibody or antigen (another type of receptor or ligand) and, furthermore, by changing their concentrations, one can obtain particle conjugates with, for the application, suitable properties.

Examples of applications of the reagent according to the invention are in ELISA (ref. 1 and 2), in immunohistochemical studies (Avrameas, Histochem. J. vol. 4, page 321, 1972; ref. 7) immunoblotting (Tsang et al, Meth. Enzymol. vol. 92, page 377; ref. 8) in microscopical studies, for the detection of antibodies in cell cultures etc.

As examples of techniques where the reagent according to the invention, can be used, are competitive and noncompetitive ELISA-methods and in USERIA (Meth. Enzymol. vol. 73, page 383 Hsu et al; ref. 9). The soluble enzyme conjugates that have been used earlier in these methods are consequently replaced with the reagents according to the present invention. Otherwise, the techniques when carrying out the assays are identical or similar with the literature described EIA-techniques (ref. 1.2 etc.). Some examples of ELISA principles with which the reagent according to the invention can be used are shown in the annexed schemes (page 5, where L is the analyte, that is the component which will be determined; Ab is antibody or lectin, carbohydrate, coenzyme etc., with specific affinity to L; E is enzyme; S is enzyme substrate and P is product, which is detected; $L_m$-●-$E_n$, and $Ab_m$-●-$E_n$ symbolise examples of reagents according to the invention; -●- is the particle, and ■ is the solid phase).

In references 1 and 2 given above (and references given in these articles) the ELISA-techniques with soluble enzyme conjugates are explained extensively, as well as the buffers and other reagents involved and the applications, and the techniques and the applications when using the reagent according to the invention are similar or identical.

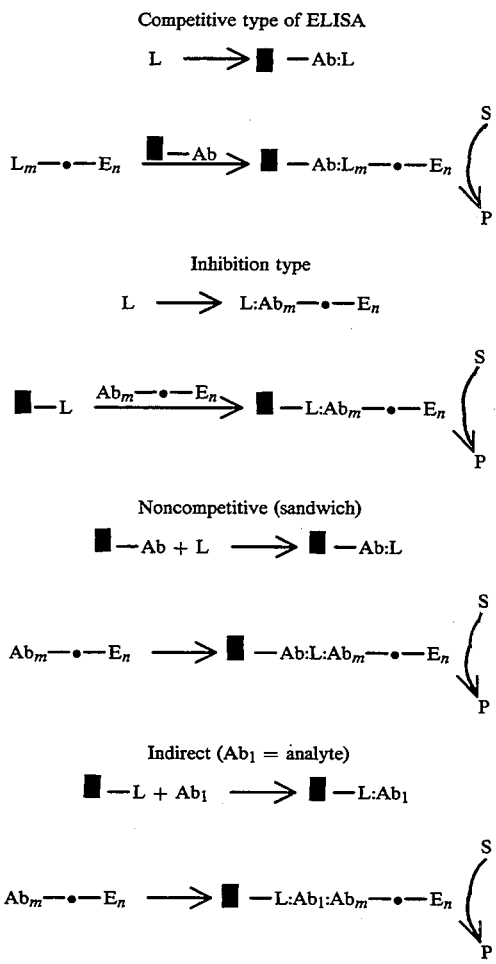

The reagent according to the invention can also be used together with many of the amplification techniques described for ELISA (avidin-biotin, enzyme-cascade, USERIA etc.). Thus, as an example, with avidin-biotin, avidin (A) and enzyme (E) can be coupled to the particles ( ) and the resulting reagent can be used for the detection of bound biotin-labelled antibody or analyte and, for example, the final complexes shown in the annexed scheme can be detected.

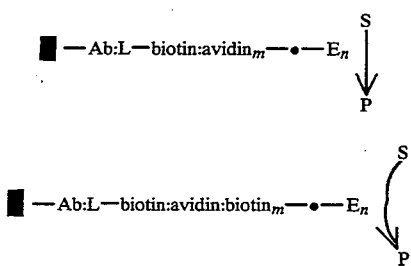

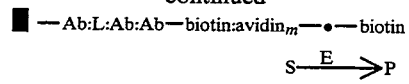

For review articles on avidin-biotin, see HSU et al page 467 in Ngo and Lenhoff (ref. 1) and Wilchek and Bayer, Immunology Today, vol. 5, page 39, 1984 (ref. 11). The sensitivity can be increased, by further reacting the product P, formed in the above enzyme reactions with other enzymes (according to for example ref. 5 above) or by transforming P to a luminescent substance according to for example Wannlund and Deluca, Meth. Enzymol. vol. 92, page 426 (ref. 12).

The final product is preferably detected with conventional ELISA-technique, that is by the eye, by measuring the absorbance, fluorescence, etc. or the reaction is followed kinetically (Tsang et al, Meth. Enzymol. vol. 92, page 391; ref. 13). Furthermore, the product P can be radioactive and can be separated from the substrate with for example a Sephadex-column and be quantified with a scintillation counter (USERIA; ref. 9 above). The above constitutes only examples of how the invention may be used in actual practice and are not intended to limit the scope of the invention. The same is valid for the following examples of particle-type, conjugation chemistry, enzymes, ligands or receptors, type of samples and components and types of solid phases that can be used in the application of the invention.

The particles can consist of a polymer substance which is insoluble in water and can consist of natural, semisynthetic or synthetic materials. As examples one can mention silicates, borosilicates, zeolites, aluminates, inorganic particles, the surface of which have been modified with organic materials containing for example alkyl groups, aromatic groups, hydroxyl groups, epoxy groups, aldehyde groups, esters, plastics (polyvinylalcohol, polystyrene, etc.), copolymers (e.g. Eupergit and Dynospheres) cross-linked polysaccharides, liposomes, artificial cells, etc.

Immobilization of the enzyme and ligand or receptor to the particles can easily be carried out by a person skilled in the art and does not limit the scope of the invention. The surface of the particles can be more or less hydrophobic. A hydrophobic surface can be used for noncovalent binding of enzyme and ligand or receptor to the particle. Both hydrophobic (for example polystyrene particles, which can be nitrated, reduced and diazotized) and hydrophilic surfaces can be chemically modified to introduce reactive groups for covalent binding and the literature is extensive in this field. (See for instance Methods Enzymology volumes 44, 104 and 135.)

For example, diazo, cyanate, ester, tosyl or tresyl groups, aldehyde, epoxi, divinylsulphone, FMP-groups can easily be prepared. After this so called activation step, the so-called coupling of the enzyme and the ligand, simultaneously or consecutively, to the particle is carried out. After the coupling, performed at suitable pH and temperature, the particles are washed after centrifugation and the reagent can then be used in, for example, those types of EIA mentioned above. The concentration of the particles in the coupling step is kept at a suitable level to avoid crosslinked particles. The so prepared particles with bound enzyme and ligand or receptor, can eventually be size separated using e.g a Sephadex-column. The ratios ligand/enzyme or receptor/enzyme are chosen after the application. A high ratio of enzyme to receptor or ligand can give a high enzyme activity but can result in a low binding capacity. A person skilled in the art can easily decide the optimal conditions for a given situation. Eventually the enzyme can be coupled first and then the ligand or the receptor can be coupled either directly on the remaining particle surface or on the enzyme with the help of crosslinker of the type glutaraldehyde or with the help of a reagent of the type periodate. One can also according to the invention, couple a conjugate between enzyme and ligand or enzyme and receptor to the particles. One obtains an increased sensitivity with the reagent according to the invention compared to the corresponding soluble conjugate because of the multiple enzyme molecules per particle and per component in the sample.

The size of the particles is chosen with regard to the application. Preferably particles with the diameter of <500 Angstroms are used, to minimize the risk that the reagent according to the invention, is washed off after the binding step in e.g. a sandwich-ELISA. This size allows more enzyme molecules and receptors or ligand molecules to bind to each particle and also allows a homogeneous particle suspension. Examples of commercially available particles of suitable size are Degussas silica particles Aerosil. The hydrophilic Aerosilparticles can easily be silanized and activated with, for example, tresyl cloride (Nilsson and Mosbach, Meth. Enzymol. vol. 104, page 56; ref. 14) periodate, etc.

The choice of enzyme and enzyme substrate can easily be done by a person skilled in the art and does not limit the scope of the invention. All enzymes, which can be coupled to particles, can be used according to the invention. Any enzyme and substrate, which are suitable for the application can be used, and the same enzymes and substrates which have been used in ELISA, immunohistochemical studies, immunoblotting and microscopical studies can be used. Examples of enzymes which can be used are peroxidase, alkaline phosphatase, galactosidase, urease, glucose-6-phosphate dehydrogenase and luciferase. To increase enzyme activity per particle an enzyme with high turnover number and relatively low molecular weight can be used. Examples of enzyme substrates which can be used together with the reagent according to the invention, are given in references 1-13 and in relevant articles in Meth. Enzymol. volumes 70, 73 and 92.

As mentioned above, the ligand or the receptor, that is the substance which is coupled to the particle together with the enzyme, shall be able to biospecifically bind either the analyte (that is the component which is to be detected in the sample) or an antibody, another protein (lectin, avidin etc.) a coenzyme, carbohydrate etc. The substance, which is coupled to the particle together with the enzyme, can be identical with the analyte or be an analogue thereof. This substance can for instance be an antibody, a lectin, avidin, another sort of protein or glycoprotein, a carbohydrate derivative, a glycolipid, a neoglycoprotein, a steroid derivative, a coenzyme derivative, a metabolite derivative, an analogue or metabolite of a pharmaceutical preparation, a metabolite, hormone, nucleotide or a derivative thereof, another virus or cell component or a derivative thereof.

The sample, which contains the cell, virus or component, can be in the form of a fluid (tears, saliva, serum, urine, water sample, etc.) in the form of more or less solid material (tissue, nitrocellulose etc.). The cells, virus or components which can be analyzed with the reagent according to the invention, are for example pathogenic organisms such as parasites, yeast cells, bacteria, mycoplasma, virus, toxins, pharmaceutical preparations and their metabolites, other metabolites, hormones, antibodies and other proteins, steroids, prostaglandins, carbohydrates, glycoconjugates, nucleotides and biomolecules in cells, virus, on cell surfaces, in tissues or in the circulation and other cells, virus or components for instance in waste water, earth, plants, animals and food.

The solid phase used for the separation step in ELISA with the reagent according to the invention, can be of the same type that have been used in ELISA with earlier described enzyme conjugates (see e.g. pages 388–391 in Meth. Enzymol. vol. 70, 1980), plastics in the form of test-tubes, microtiter plates, particles, filters, etc., glassfiber or filters of paper, ion exchangers, agarose particles, Sephadex particles, polyacrylamid gel, bentonite, magnetic preparations of cellulose, agarose or plastics, etc. The chosen shape of the solid phase depends on the application and for instance balls, columns, dipsticks, microtiterplates, membranes, filters or test-tubes can be used.

After the separation of the bound enzyme particles from the non-bound, the activity of either the bound fraction or of the non-bound fraction is determined.

Some examples of how the invention may be used in actual practice are described in the following Examples, which in no way is intended to restrict the scope of the invention.

EXAMPLE

Activation Of Silica Particles

Silica particles from Degussa (400 mg, Aerosil TT 600) were silanized in a vacuumexciccator with γ-glycidoxypropyltrimethoxysilane (300 microliter) using trimethylamine (300 microliter) as catalyst at 140° C. for 4 hours. The procedure was repeated. The epoxy groups were hydrolysed with water and HCl (pH 3) at 90° C. for 30 minutes. Centrifugation, wash with water and gradual transfer to acetone according to ref. 14, followed by activation of the hydroxyl groups with tresyl chloride (30 microliters per 150 mg particles) in 1 ml acetone and with 40 microliters pyridine at 0° C. for 20 minutes, wash according to ref. 14, (with centrifugation of the particles), gave particles with 150 micromole tresyl groups per g particles according to elementary analysis.

Coupling of peroxidase and rabbit anti-human transferrin immunoglobulin and of peroxidase and rabbit anti-human α-1-fetoprotein immunoglobulin to tresyl-activated Aerosilparticles.

Peroxidase (12 mg, purified with affinity chromatography, Sigma) and antitransferrin (1.5 ml, dialysed with 0.3M sodium-bicarbonate, pH 8.5; Dakopatts), were slowly mixed during stirring with tresyl activated silica particles (250 mg wet-weight in 4 ml buffer) and ultrasoundtreated for 3 minutes. Coupling proceeded with agitation on an end-over-end table for 70 hours at 4° C. The particles were washed with coupling buffer (4 times) using centrifugation of the particles. Bovine serum albumin (40 mg in 5 ml) was added to block any eventually remaining tresyl groups and the particles are stored at 4° C. Spectrophotometric determination of the absorbance of the wash-solutions at 403 nm and 280 nm indicated that 2 mg peroxidase and 2 mg antitransferrin had been coupled. Peroxidase (15 mg, 1000 U/mg, Boehringer, ELISA-quality) and anti-α-1-fetoprotein immunoglobulin (50 mg, Dakopatts) were coupled at 4° C. for 40 hours in almost the same way but with 8.5 ml coupling-buffer (see above) and by the gradual addition of tresyl-activated silica particles (25 mg dry weight in 1 ml buffer). Remaining tresyl groups were blocked with Tris-HCl, pH 8.3, 0.2M.

Determination of human transferrin with sandwich-ELISA using peroxidase-antitransferrin-silica:

Step 1. A microtiterplate was incubated with 300 microliter in each well of 10 microgram rabbit antitransferrin immunoglobulin (Dakopatts, AO 61, lot 012) dissolved in PBS (10 mM sodium phosphate +145 mM NaCl, pH 7.2). Incubation at 4° C. over night. The plate was washed with PBS containing 0.1% Tween 20 and 0.5 NaCl (buffer B).

Step 2. The plate was incubated with a dilution serie (10 microgram to 0.02 ng) of human transferrin (apoform, Sigma) dissolved in buffer B. Incubation for 2 hours at 20° C.

Step 3. Peroxidase-antitransferrin-particles prepared as above were suspended in buffer B and added to the wells. Incubation for 3 hours at 20° C. with gentle agitation on a shaker. The plate was washed 3 times with buffer B and substrate solution (150 microliter of 8 mg 1,2-phenylenediamine dihydrochloride dissolved in 0.1M citric acid/phosphate buffer pH 5.0, 12 ml, and 12 microliter $H_2O_2$) was added to the wells (step 4).

After 50 minutes the absorbance of the wells was measured with a multiscanner at 492 nm. The wells which in step 2 were incubated with less than 2 ng transferrin gave higher absorbance than the background absorbance (obtained in wells which in step 2 were incubated without antigen, that is, with only buffer B). Determination of human α-1-fetoprotein with sandwich-ELISA using peroxidase-anti-α-1-fetoprotein-silica:

Human α-1-fetoprotein (Dakopatts, X 900 standard, lot 014) was determined with same procedure and buffers used in the above example but with the difference that silica particles with co-immobilised peroxidase and anti-α-1-fetoprotein immunoglobulin (prepared as described above) were used. In step 1 the wells were incubated with anti-α-1-fetoprotein immunoglobulin (rabbit, Dakopatts, A008, lot 085) and in step 2 α-1-fetoprotein was added to the wells in a dilution serie from 1 microgram to 0.1 ng. In step 3 soluble conjugate of peroxidase and antihuman α-1-fetoprotein was used (rabbit, Dakopatts, P 128, lot 046) for comparison with the silica conjugate. Wells, that in step 2 were incubated with 0.1 ng antigen and in step 3 incubated with enzyme-antibody-particles gave absorbance which was more than twice as high as the background absorbance (obtained in wells where no antigen was incubated in step 2). The soluble enzyme-antibody conjugate gave no absorbance difference for 0.1 ng antigen. Both soluble and particle bound conjugate gave ca. 10 times higher absorbance in wells which in step 2 were incubated with 1 microgram antigen compared to the absorbance obtained in the blank wells.

I claim:

1. A method for determining the presence of a component in a sample, said method comprising
   (a) adding said sample to a solid support having bound thereon a biomolecule which specifically binds said component,
   (b) adding a reagent comprising at least one enzyme and at least one other substance both of which are covalently or noncovalently bound to a particle, said particle having no solubility in water under the conditions employed in the method of preparing or use of said reagent, wherein said particle is smaller than or equal to 1000 Å (A.U.) in diameter, and wherein said substance is capable of specifically binding said component,
   (c) washing away said reagent which does not bind to said component,
   (d) adding a substrate for said enzyme, and
   (e) detecting the reaction product of said substrate and said enzyme as an indication of the presence of said component in said sample.

2. The method according to claim 1, wherein said particle is smaller than 500 Angstroms in diameter.

3. The method according to claim 2, wherein said particle is 400 Angstroms in diameter.

4. A method for determining the presence of human transferrin in a sample, said method comprising
   (a) adding said sample to a solid support having bound thereon antitransferrin immunoglobulin,
   (b) adding a reagent comprising peroxidase and anti-human transferrin immunoglobulin both of which are covalently or noncovalently bound to a particle, said particle having no solubility in water under the conditions employed in the method of preparing or use of said reagent, wherein said particle is smaller than or equal to 1000 Å (A.U.) in diameter,
   (c) washing away said reagent which does not bind to said human transferrin,
   (d) adding a substrate for said peroxidase, and
   (e) detecting the reaction product of said peroxidase and said substrate as an indication of the presence of said human transferrin in said sample.

5. The method according to claim 4, wherein said particle is smaller than 500 Angstroms in diameter.

6. The method according to claim 5, wherein said particle is 400 Angstroms in diameter.

7. A method for determining the presence of human α-1-fetoprotein in a sample, said method comprising
   (a) adding said sample to a solid support having bound thereon anti-α-1-fetoprotein immunoglobulin,
   (b) adding a reagent comprising peroxidase and anti-human α-1-fetoprotein immunoglobulin both of which are covalently or noncovalently bound to a particle, said particle having no solubility in water under the conditions employed in the method of preparing or use of said reagent, wherein said particle is smaller than or equal to 1000 Å (A.U.) in diameter,
   (c) washing away said reagent which does not bind to said human α-1-fetoprotein,
   (d) adding a substrate for said peroxidase, and
   (e) detecting the reaction product of said peroxidase and said substrate as an indication of the presence of said human α-1-fetoprotein in said sample.

8. The method according to claim 7, wherein said particle is smaller than 500 Angstroms in diameter.

9. The method according to claim 8, wherein said particle is 400 Angstroms in diameter.

10. A method for determining the presence of a component in a sample, said method comprising (a) adding said sample to a solid support having bound thereon a biomolecule which specifically binds said component,
(b) adding an antibody which specifically binds said component,
(c) adding a reagent comprising at least one enzyme and at least one other substance both of which are covalently or noncovalently bound to a particle, said particle having no solubility in water under the conditions employed in the method of preparing or use of said reagent, wherein said particle is smaller than or equal to 1000 Å (A.U.) in diameter, and wherein said substance is capable of specifically binding said antibody,
(d) washing away said reagent which does not bind to said antibody,
(e) adding a substrate for said enzyme, and
(f) detecting the reaction product of said substrate and said enzyme as an indication of the presence of said component in said sample.

11. A method for determining the presence of a component in a sample, said method comprising
(a) adding said sample to a solid support having bound thereon a biomolecule which specifically binds said component,
(b) adding a protein which specifically binds said component,
(c) adding a reagent comprising at least one enzyme and at least one other substance, both of which are covalently or noncovalently bound to a particle, said particle having no solubility in water under the conditions employed in the method of preparing or use of said reagent, wherein said particle is smaller than or equal to 1000 A (A.U.) in diameter, and wherein said substance is capable of specifically binding said protein,
(d) washing away said reagent which does not bind to said protein,
(e) adding a substrate for said enzyme, and
(f) detecting the reaction product of said substrate and said enzyme as an indication of the presence of said component in said sample.

* * * * *

UNITED STATES PATENT AND TRADEMARK OFFICE
CERTIFICATE OF CORRECTION

PATENT NO. : 5,405,752
DATED : April 11, 1995
INVENTOR(S) : Kurt G. Nilsson

It is certified that error appears in the above-indentified patent and that said Letters Patent is hereby corrected as shown below:

On the title page, item:

[22] PCT Filed: October 2, 1989

[86] PCT No.: PCT/SE89/00539

Section 371 Date: August 1, 1990

Section 102(e) Date: August 1, 1990

[87] PCT Pub. No.: WO90/04181

PCT Pub. Date: April 19, 1990

Signed and Sealed this

Thirtieth Day of May, 1995

Attest:

BRUCE LEHMAN

*Attesting Officer*    *Commissioner of Patents and Trademarks*